United States Patent
Kim et al.

(10) Patent No.: US 11,987,816 B2
(45) Date of Patent: May 21, 2024

(54) COMPOSITION FOR INDUCING DEDIFFERENTIATION FROM SOMATIC CELLS TO INDUCED PLURIPOTENT STEM CELLS AND METHOD OF INDUCING DEDIFFERENTIATION USING SAME

(71) Applicant: KOREA UNIVERSITY RESEARCH AND BUSINESS FOUNDATION, Seoul (KR)

(72) Inventors: Byoung Soo Kim, Seoul (KR); Seung Jin Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 744 days.

(21) Appl. No.: 17/043,836

(22) PCT Filed: Apr. 2, 2019

(86) PCT No.: PCT/KR2019/003898
§ 371 (c)(1),
(2) Date: Sep. 30, 2020

(87) PCT Pub. No.: WO2019/194549
PCT Pub. Date: Oct. 10, 2019

(65) Prior Publication Data
US 2021/0403877 A1    Dec. 30, 2021

(30) Foreign Application Priority Data

Apr. 2, 2018  (KR) .................. 10-2018-0038371
Jul. 23, 2018  (KR) .................. 10-2018-0085476

(51) Int. Cl.
*C12N 5/074* (2010.01)

(52) U.S. Cl.
CPC ...... *C12N 5/0696* (2013.01); *C12N 2501/604* (2013.01); *C12N 2501/606* (2013.01); *C12N 2501/998* (2013.01); *C12N 2502/025* (2013.01); *C12N 2506/025* (2013.01); *C12N 2506/28* (2013.01); *C12N 2533/54* (2013.01)

(58) Field of Classification Search
CPC ............ C12N 5/0696; C12N 2501/604; C12N 2501/606; C12N 2501/998; C12N 2502/025; C12N 2506/025; C12N 2506/28; C12N 2533/54; C12N 2501/2308
See application file for complete search history.

(56) References Cited

U.S. PATENT DOCUMENTS 9,580,682 B1   2/2017  Kim et al.
2009/0047263 A1   2/2009  Yamanaka et al.
2017/0044493 A1   2/2017  Kim et al.

FOREIGN PATENT DOCUMENTS

| CN | 1541113 A | 10/2004 |
|---|---|---|
| CN | 101541767 A | 9/2009 |
| KR | 10-2011-0078234 A | 7/2011 |
| KR | 10-1395214 B1 | 5/2014 |
| KR | 10-2017-0019696 A | 2/2017 |
| KR | 10-2017-0019697 A | 2/2017 |
| WO | WO-9218641 A1 | 10/1992 |
| WO | WO-2002-087627 A1 | 11/2002 |
| WO | WO-2008-061740 A1 | 5/2008 |
| WO | WO-2015-160982 A1 | 10/2015 |
| WO | WO-2016-076507 A1 | 5/2016 |

OTHER PUBLICATIONS

Cevallos et al, scientific reports, (2020) 10:19710) (Year: 2020).*
Lee et al, Stem cells and Dev, V 29, N 3, 2020) (Year: 2020).*
Smith et al, Jour Cell Phys, 220: 21-29, 2009). (Year: 2009).*
ESR of EP Patent Application No. 19782003.8, issued on May 11, 2021.
Jung, J., et al.; "CXCR2 and Its Related Ligands Play a Novel Role in Supporting the Pluripotency and Proliferation of Human Pluripotent Stem Cells", Stem Cells and Development, vol. 24, No. 8, 2015, pp. 948-961.
Jung, J., et al.; "CXCR2 Inhibition in Human Pluripotent Stem Cells Induces Predominant Differentiation to Mesoderm and Endoderm Through Repression of mTOR, β-Catenin, and hTERT Activities", Stem Cells and Development, vol. 25, No. 13, 2016, pp. 1006-1019.
Chen, T., et al.; "Rapamycin and other longevity-promoting compounds enhance the generation of mouse induced pluripotent stem cells", Aging Cell, 2011, 10, pp. 908-911.
Park, Y., et al. "Human Feeder Cells Can Support the Undifferentiated Growth of Human and Mouse Embryonic Stem Cells Using Their Own Basic Fibroblast Growth Factors", Stem Cells and Development, vol. 20, No. 11,2011, pp. 1901-1910.
Lee, S., et al.; "CXCR2 Ligands and mTOR Activation Enhance Reprogramming of Human Somatic Cells to Pluripotent Stem Cells", Stem Cells and Development, vol. 29, No. 3, 2020, pp. 119-132.
Kim, B.S. (2017) "Production of Conditioned Medium Derived from Standardization Human Cell for Complete Feeder Free Culture of Human iPSCs and Its Mechanism Study.", Ministry of Science and ICT. Bio. Medical Technology Development Business, Research Report. pp. 1-32, (Nov. 13, 2017), with English translation.
International Search Report from corresponding PCT Application No. PCT/KR2019/003898, dated Jul. 31, 2019, with English translation.
Office Action from correspinding Chinese Patent Application No. 201980036893.6, dated Aug. 17, 2022.

* cited by examiner

*Primary Examiner* — Emily A Cordas
*Assistant Examiner* — Constantina E Stavrou
(74) *Attorney, Agent, or Firm* — Harness, Dickey & Pierce, P.L.C.

(57) ABSTRACT

The present invention relates to a composition for inducing dedifferentiation form somatic cells to induced pluripotent stem cells (iPSs) and method of inducing dedifferentiation using same, wherein the composition for inducing dedifferentiation and the method of inducing dedifferentiation increases the efficiency of dedifferentiation from somatic cells to iPSs by stimulating CXC chemokine receptor 2 (CXCR2), which is a receptor on human somatic cells, and thus may be effectively used for inducing the dedifferentiation to iPSs.

4 Claims, 18 Drawing Sheets

Specification includes a Sequence Listing.

SEQUENCE LISTING

```
<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: IL-8 forward primer

<400> SEQUENCE: 1
ctggccgtgg ctctcttg                                              18

<210> SEQ ID NO 2
<211> LENGTH: 20
<212> TYPE: DNA
<213> ORGANISM: Artificial Sequence
<220> FEATURE:
<223> OTHER INFORMATION: IL-8 reverse primer

<400> SEQUENCE: 2
ccttggcaaa actgcacctt                                            20

<210> SEQ ID NO 3
<211> LENGTH: 57
<212> TYPE: DNA
<213> ORGANISM: Artificial Sequence
<220> FEATURE:
<223> OTHER INFORMATION: shRNA lentiviral particles

<400> SEQUENCE: 3
gatccgtcta ctcatccaat gttattcaag agataacatt ggatgagtag acttttt    57

<210> SEQ ID NO 4
<211> LENGTH: 57
<212> TYPE: DNA
<213> ORGANISM: Artificial Sequence
<220> FEATURE:
<223> OTHER INFORMATION: shRNA lentiviral particles

<400> SEQUENCE: 4
gatcccctca agattctagc tatattcaag agatatagct agaatcttga ggttttt    57
```

```
<210> SEQ ID NO 5
<211> LENGTH: 57
<212> TYPE: DNA
<213> ORGANISM: Artificial Sequence
<220> FEATURE:
<223> OTHER INFORMATION: shRNA lentiviral particles

<400> SEQUENCE: 5
gatccgccac taaattgaca cttattcaag agataagtgt caatttagtg gcttttt          57

<210> SEQ ID NO 6
<211> LENGTH: 23
<212> TYPE: DNA
<213> ORGANISM: Artificial Sequence
<220> FEATURE:
<223> OTHER INFORMATION: CXCR2 forward primer

<400> SEQUENCE: 6
caatgaatga atgaatggct aag                                               23

<210> SEQ ID NO 7
<211> LENGTH: 25
<212> TYPE: DNA
<213> ORGANISM: Artificial Sequence
<220> FEATURE:
<223> OTHER INFORMATION: CXCR2 reverse primer

<400> SEQUENCE: 7
aaagttttca aggttcgtcc gtgtt                                             25
```

COMPOSITION FOR INDUCING DEDIFFERENTIATION FROM SOMATIC CELLS TO INDUCED PLURIPOTENT STEM CELLS AND METHOD OF INDUCING DEDIFFERENTIATION USING SAME

CROSS-REFERENCE TO RELATED APPLICATIONS

This application is a national phase application of PCT Application No. PCT/KR2019/003898, filed on Apr. 2, 2019, which claims priority to Korean Patent Application No. 10-2018-0085476, filed on Jul. 23, 2018 and Korean Patent Application No. 10-2018-0038371, filed on Apr. 2, 2018. The entire disclosures of the applications identified in this paragraph are incorporated herein by references.

FIELD

The present invention was made by project number 2017M3A9C6027001 under the support of the Ministry of Science and Technology of the Republic of Korea. The research management institution for the above project is the Korea Research Foundation, the name of the research project is "Bio. Medical Technology Development Project", and the name of the research project is "Direct Cross Differentiation Human Neural Stem Cell Culture Production Technology Optimization and Stability Study". The host institution is Korea University, and the research period is from Apr. 1, 2017 to Mar. 31, 2021.

The present disclosure relates to a composition for inducing dedifferentiation from a somatic cell to an induced pluripotent stem cell (iPS) and, more particularly, to a dedifferentiation-inducing composition capable of promoting or inhibiting dedifferentiation efficiency by stimulating CXCR2 (CXC chemokine receptor 2), which is a receptor on a human somatic cell and a dedifferentiation inducing method using the same.

BACKGROUND

The production of a stem cell therapy product indispensably requires in vitro mass culture of a stem cell, which is a source therefor, with the safety and economical benefit of the cultured stem cell requisite for clinical application as the cell therapy product.

Nowadays, however, a human pluripotent stem cell needs an animal-derived feeder cell for the proliferation and culture thereof or employs a vessel coated with a special gel containing an animal-derived product for the growth thereof. Thus, there is an ever-present danger of contamination with heteroproteins, which leads to a concern with safety, and the employment of an expensive special gel is not economically adequate for mass production of the cell therapy product.

Attempts have been made to use versatile viruses, chemicals, cytokines, etc. in increasing the production efficiency of a dedifferentiated stem cell that could be clinically applied in future. For example, Sendai virus is used so as to prevent integration into host chromosomes or there are studies taking advantage of fusion protein transduction or mRNA.

In relation to conventional preparation methods for an induced pluripotent stem cell (iPS) by reprogramming, there is the problem of low efficiency that only about 10 iPSs are obtained from as many as $5\times10^4$ human dermal fibroblast cells.

SUMMARY

Technical Problem

As a result of thorough and intensive research, the present inventors found that an excellent efficiency of dedifferentiation into an induced pluripotent stem cell (iPS) can be obtained when somatic cells transformed with CXCR2 (CXC chemokine receptor 2) ligand is dedifferentiated and when dedifferentiation is made in a somatic cell in which the expression level of CXCR2 has been increased by transformation.

A purpose of the present disclosure is to provide a composition for dedifferentiation from a somatic cell containing CXCR2 or a ligand thereof to an induced pluripotent stem cell.

Another purpose of the present disclosure is to provide a placenta-derived cell conditioned medium for dedifferentiating a somatic cell containing CXCR2 or a ligand thereof to an induced pluripotent stem cell.

A further purpose of the present disclosure is to provide a method for dedifferentiation from a somatic cell to an induced pluripotent stem cell, the method comprising:
  a somatic cell transformation step of increasing the expression of CXCR2; and
  a somatic cell culturing step of culturing the transformed somatic cell.

A still further purpose of the present disclosure is to provide a use of a cell culture composition comprising a CXCR2 ligand in dedifferentiating a somatic cell to an induced pluripotent stem cell.

Technical Solution

The present disclosure relates to a composition for inducing dedifferentiation from a somatic cell to an induced pluripotent stem cell (iPS). The dedifferentiation-inducing composition and the dedifferentiation-inducing method using the same according to the present disclosure increase an efficiency of dedifferentiation from a somatic cell to an induced pluripotent stem cell by stimulating CXCR2 (CXC chemokine receptor 2), which is a receptor on a human somatic cell.

Thorough and intensive research conducted by the present inventors results in the finding that dedifferentiation into an induced pluripotent stem cell (iPS) was conducted at increased efficiency when a somatic cell was cultured in a medium containing a CXCR2 ligand and when CXCR2 expression was upregulated through transformation, but at decreased efficiency when the expression of CXCR2 in the somatic cell was downregulated.

Below, a detailed description will be given of the present disclosure.

An aspect of the present disclosure pertains to a composition for inducing dedifferentiation from a somatic cell containing CXCR2 or a ligand thereof to an induced pluripotent stem cell.

CXC chemokine receptors are an integral membrane protein that specifically bind and respond to cytokines of the CXC chemokine family. Among them, CXCR2 is a closely related receptor that recognizes CXC chemokines that possess an E-L-R amino acid motif immediately adjacent to the CXC motif thereof. Chemokines are a family of cytokine proteins known to induce directed chemotaxis.

The ligand of CXCR2 may be at least one selected from the group consisting of GRO-α (growth-regulated oncogene-α), GRO-β (growth-regulated oncogene-β), GRO-γ

(growth-regulated oncogene-γ), GCP-2 (granulocyte chemotactic protein-2), NAP-2 (Neutrophil Activating Peptide-2), ENA-78 (Epithelial neutrophil-activating protein-78), and IL-8 (Interleukin-8) and may be, for example, GRO-α or IL-8, but is not limited thereto.

The somatic cell may be at least one selected from the group consisting of endothelial cells, epithelial cells, and placenta cells.

Another aspect of the present disclosure pertains to a placenta-derived cell conditioned medium comprising a ligand of CXCR2 for inducing dedifferentiation from a somatic cell to an induced pluripotent stem cell.

As used herein, the term "placenta-derived cell conditioned medium" refers to a medium prepared by inoculating placenta-derived cells into a gelatin-coated well plate, adding a cell culture to the plate to culture the placenta-derived cells, and collecting the supernatant only. When used, the human placenta-derived feeder cells were found to allow human embryonic stem cells to remain undifferentiated and thus have arisen for the utility thereof.

The ligand of CXCR2 may be at least one selected from the group consisting of GRO-α, GRO-β, GRO-γ, GCP-2, NAP-2, ENA-78, and IL-8 and may be, for example, GRO-α or IL-8, but is not limited thereto.

The somatic cell may be at least one selected from the group consisting of endothelial cells, epithelial cells, and placenta cells.

The placenta-derived cell may be a placenta-derived fibroblast-like cell that is isolated from human chorionic plate and cultured.

The placenta-derived cell conditioned medium may contain human placenta-derived cells cultured in a cell growth medium.

A further aspect of the present disclosure pertains to a method for inducing dedifferentiation from a somatic cell to an induced pluripotent stem cell (iPS), the method comprising:
  a somatic cell transformation step of increasing expression of CXCR2; and
  a somatic culture step of culturing the transformed somatic cell.

In the somatic cell transformation step, a CRISPR/Cas nuclease system or lentiviral activation particles may be used.

As used herein, the term "lentivirus" refers to a genus of retroviruses, a kind of RNA viruses which translocate into the nucleus of a host cell and integrate into the host DNA to express the viral cDNA and produce viral particles. Lentivirus is used as a vector for regulating gene expression by virtue of taking advantage of such mechanisms.

In an embodiment of the present disclosure, the somatic cell transformation step may be conducted by infecting CXCR2 lentiviral activation particles into a somatic cell to upregulate CXCR2 expression therein.

The somatic cell may be at least one selected from the group consisting of an endothelial cell, an epithelial cell, and a placenta cell.

The culture may be performed in a placenta-derived cell conditioned medium.

The placenta-derived cell may be a placenta-derived fibroblast-like cell that is isolated from human chorionic plate and cultured.

The placenta-derived cell conditioned medium may contain human placenta-derived cells cultured in a cell growth medium.

The dedifferentiation induction method may further comprise a stem cell isolation step of isolating a stem cell from the colony formed in the somatic cell culture step.

Advantageous Effects

The present invention relates to a composition for inducing dedifferentiation from a somatic cell to an induced pluripotent stem cell (iPS) and a dedifferentiation induction method using same. The dedifferentiation induction composition and method stimulate the human somatic cell receptor CXCR2 (CXC chemokine receptor 2) to increase efficiency of the dedifferentiation from somatic cells to induced pluripotent stem cells, finding effective applications in inducing dedifferentiation to induced pluripotent stem cells.

DETAILED DESCRIPTION

The present disclosure provides a composition for inducing dedifferentiation from a somatic cell to an induced pluripotent stem cell (iPS), the composition comprising CXCR2 (CXC chemokine receptor 2) or a ligand thereof, a placenta-derived cell conditioned medium for inducing dedifferentiation, and a method for inducing differentiation, in which CXCR2 is overexpressed by transformation.

Examples

A better understanding of the present disclosure may be obtained through the following examples which are set forth to illustrate, but are not to be construed as limiting the present invention.

Example 1: Assay for Expression of GRO-α and IL-8 in Endothelial Cells, Epithelial Cells, and Placenta Cells Primary umbilical endothelial cells (HUVEC) were purchased as the human endothelial cells from ATCC. An endothelial cell growth medium (LONZA), which contains 2% fetal bovine serum (FBS) and vascular endothelial growth factor (VEGF), was purchased. Cells were cultured in an incubator maintained at 37° C. in a 5% $CO_2$ atmosphere.

Primary dermal fibroblasts (HDF) were purchased as the human epithelial cells from ATCC and cultured in a medium containing 90% Dulbecco's modified Eagle's medium (DMEM) and 10% FBS in a 5% $CO_2$ incubator maintained at 37° C.

Cells isolated from chorionic plate were used as the human placenta cells (HPC) and the isolated placenta cells were cultured in DMEM supplemented 10% FBS in a 5% $CO_2$ incubator maintained at 37° C.

In order to measure secretion levels of GRO-α and IL-8 therefrom, the endothelial cells, the epithelial cells, and the placenta cells were each cultured in culture dishes for 24, 48, and 72 hours and the culture media were collected and subjected to enzyme immunoassay to determine secretion levels of GRO-α and IL-8 with time.

In brief, the experiment was preformed using a kit (Human ELISA kit, Abcam). As for the experiment process, 100 μl of each of the samples was incubated overnight at 4° C. and then incubated with a biotin antibody for one hours. After reaction with a streptavidin solution and a reagent (TMB One-Step Substrate Reagent), 50 μl of a stop solution was added to each of the sample to terminate the reaction. Absorbance was read at 450 nm on a microplate reader.

Figure 1A:
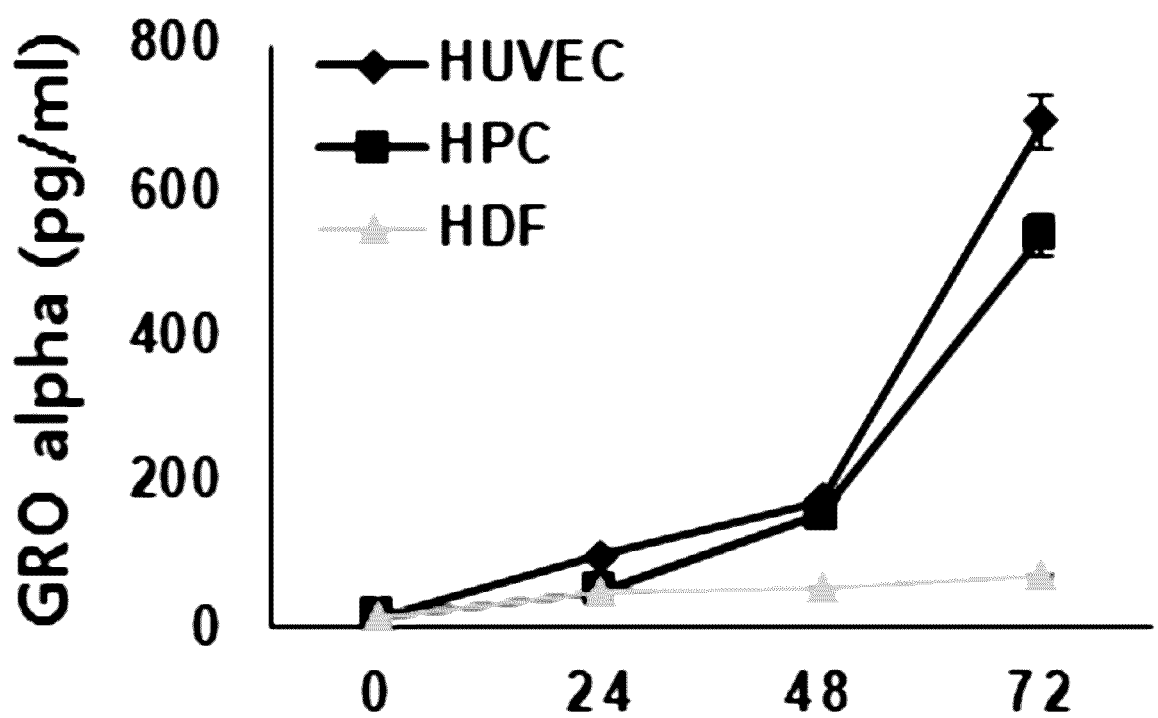
FIG. 1A shows changes in expression levels of GRO-α (growth-regulated oncogene-α) in endothelial cells, epithelial cells, and placenta cells with culture time as measured by enzyme immunoassay.

As can be seen in FIG. 1a and Table 1, GRO-α was expressed at higher levels in placenta cells and endothelial cells, especially in endothelial cells than in epithelial cells.

TABLE 1

| Time (hour) | Endothelial cell (HUVEC) | Epithelial cell (HDF) | Placenta cell (HPC) |
| --- | --- | --- | --- |
| 0 | 15.13 | 15.91 | 13.69 |
| 24 | 95.64 | 47.91 | 49.60 |
| 48 | 173.52 | 152.35 | 53.81 |
| 72 | 693.35 | 538.40 | 70.92 |

Figure 1B:
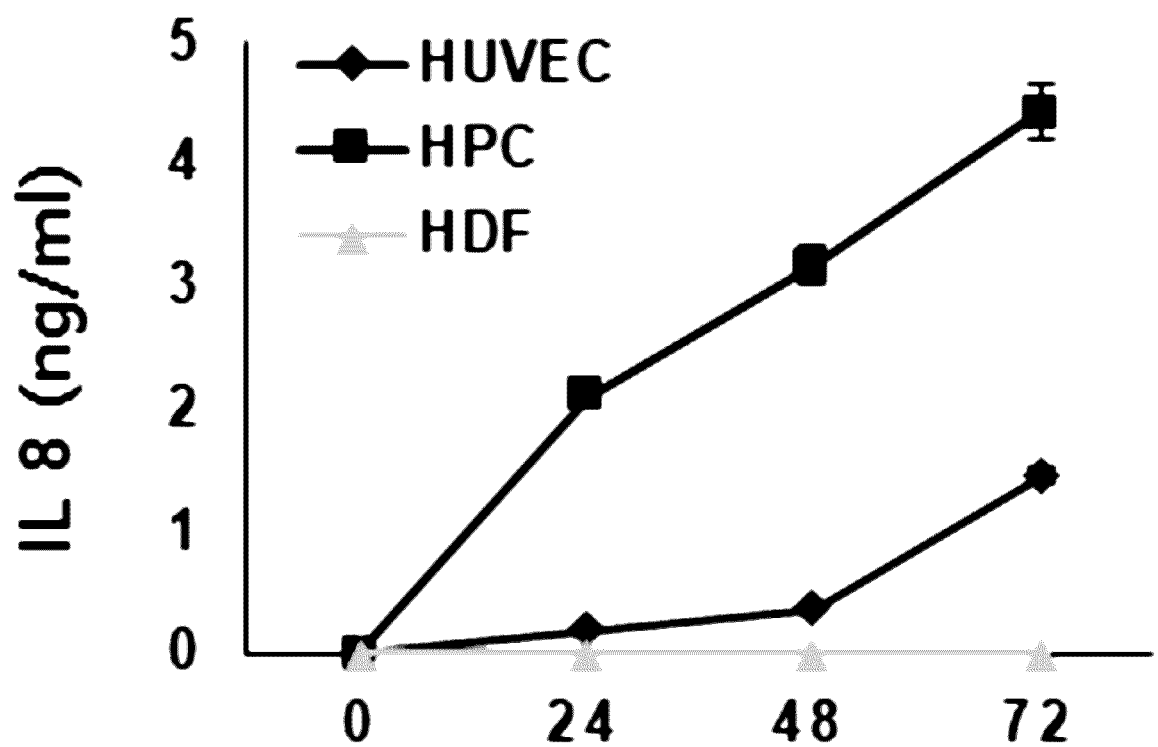
FIG. 1B shows changes in expression levels of IL-8 (Interleukin-8) in endothelial cells, epithelial cells, and placenta cells with culture time as measured by enzyme immunoassay.

As can be seen in FIG. 1b and Table 2, higher expression levels of IL-8 were detected in placenta cells than in epithelial cells and endothelial cells.

TABLE 2

| Time (hour) | Endothelial cell (HUVEC) | Epithelial cell (HDF) | Placenta cell (HPC) |
| --- | --- | --- | --- |
| 0 | 0.00 | 0.00 | 0.00 |
| 24 | 0.19 | 2.11 | 0.00 |
| 48 | 0.36 | 3.17 | 0.00 |
| 72 | 1.45 | 4.42 | 0.00 |

The endothelial cell, epithelial cells, and placenta cells cultured in culture dishes were assayed for the expression of GRO-α by fluorescent staining.

Briefly, the cultured cells were fixed with 4% formalin at room temperature for 10 minutes, permeabilized with 0.1% Triton X-100/PBS for 10 minutes, and then incubated overnight with a primary antibody to GRO-α (Abcam #ab86436) at 4° C. On the next day, incubation with the secondary antibody Alexa Fluor® 488 at room temperature for one hour was followed by treatment with 4',6-diamindino-2-phenylindone (DAPI) for 5 minutes in a dark condition before fluorescence microscopy to measure the expression of GRO-α in the cells.

Figure 1C:
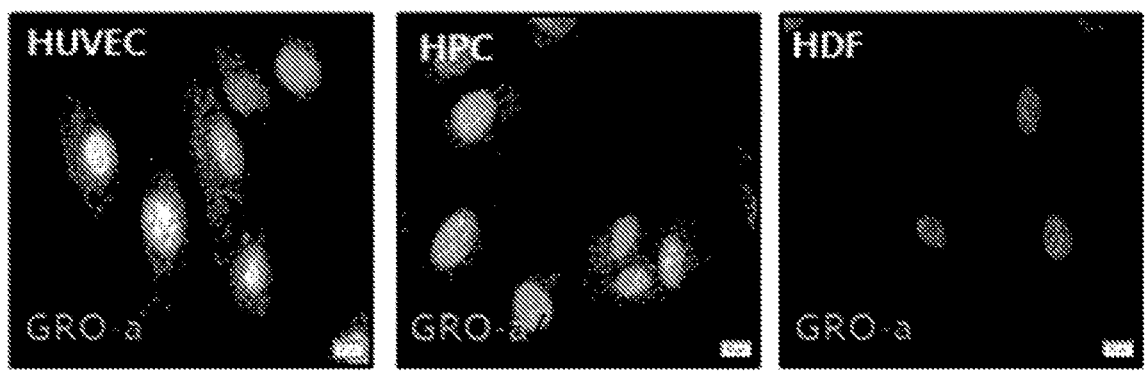
FIG. 1C shows comparison of GRO-α expression in cultured endothelial cells, epithelial cells, and placenta cells by immunofluorescence staining.

As shown in FIG. 1c, higher expression levels of GRO-α were detected in endothelial cells than in epithelial cells and placenta cells.

The expression of IL-8 gene in endothelial cells, epithelial cells, and placenta cells was compared and analyzed using real-time polymerase chain reaction. With the aid of a kit (Qiagen RNeasy kit, Qiagen Hilden, Germany), RNA was isolated from the differentiation-induced cells. In the presence of a reverse transcriptase (Superscript II reverse transcriptase, Gibco) and oligo(dT), 2 μg of RNA was used to synthesize cDNA.

For assay, the synthesized cDNAs were each polymerized using primers for IL-8 gene and a master mix (iQ SYBR Green qPCR Master Mix) in an apparatus (Bio-Rad iCycler iQ system, Bio-Rad Laboratories, USA). The assay values were normalized using GAPDH gene, and P values were used to determine statistical significance (*$P=0.05$). Primers for IL-8 gene expression assay are as listed in Table 3, below.

TABLE 3

| SEQ ID NO: | Name | Sequence |
|---|---|---|
| 1 | IL-8 forward primer | CTGGCCGTGG CTCTCTTG |
| 2 | IL-8 reverse primer | CCTTGGCAAAA CTGCACCTT |

Figure 1D:
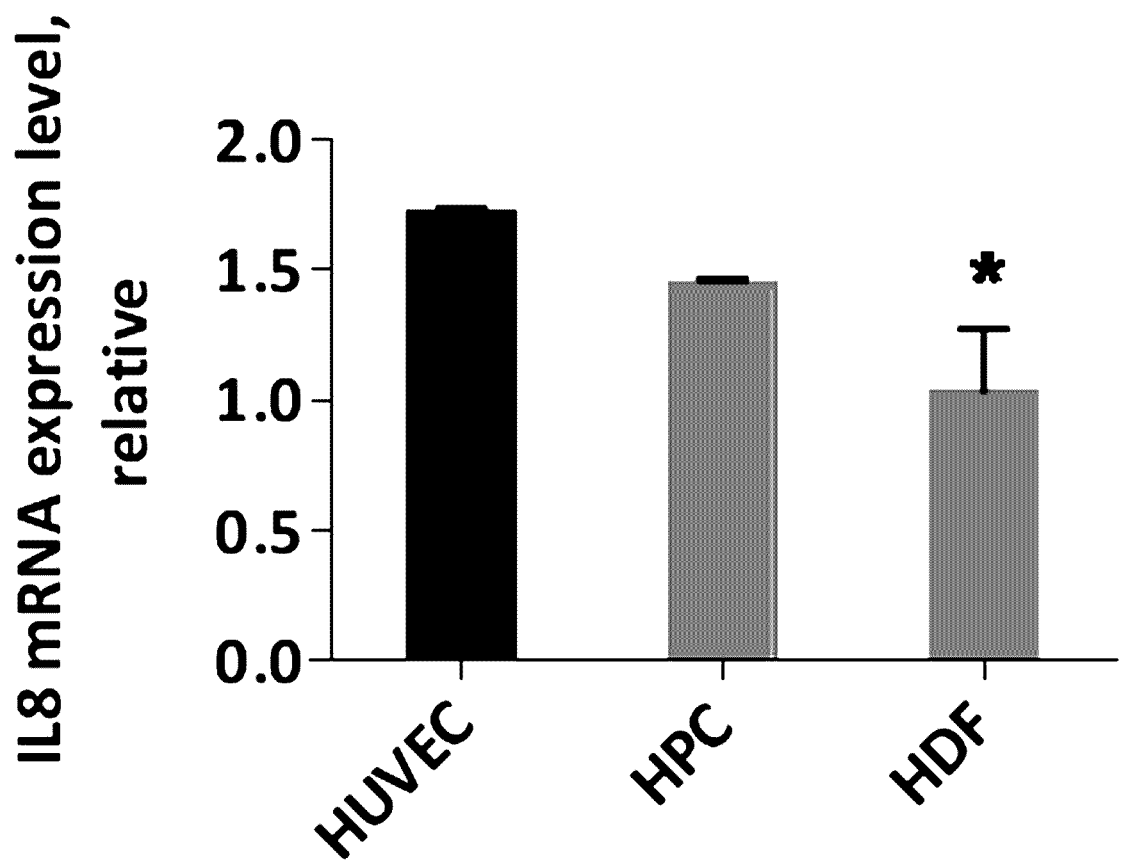
FIG. 1D shows comparison of IL-8 expression in cultured endothelial cells, epithelial cells, and placenta cells at mRNA levels.

As is understood from the data of FIG. 1d and Table 4, endothelial cells expressed GRO-α at higher levels than epithelial cells and placenta cells.

TABLE 4

| | Endothelial cell (HUVEC) | Epithelial cell (HDF) | Placenta cell (HPC) |
|---|---|---|---|
| Relative mRNA expression level of IL-8 | 1.72 | 1.45 | 1.03 |

As a consequence, GRO-α and IL-8 were expressed at the highest levels in endothelial cells and stimulated CXCR2, leading to dedifferentiation of endothelial cells at higher efficiencies than epithelial cells and placenta cells.

Example 2: Comparison of Dedifferentiation Efficiency Among Endothelial Cell, Epithelial Cell, and Placenta Cell Through alkaline phosphatase staining, an examination was made to see whether the stem cells dedifferentiated from the somatic cells in Example 1 possessed self-renewal, an ability typical characteristic for induced pluripotent stem cells. Alkaline phosphatase (ALP) staining was conducted using a kit (ES Cell Characterization kit, Chemicon International).

Figure 2A:
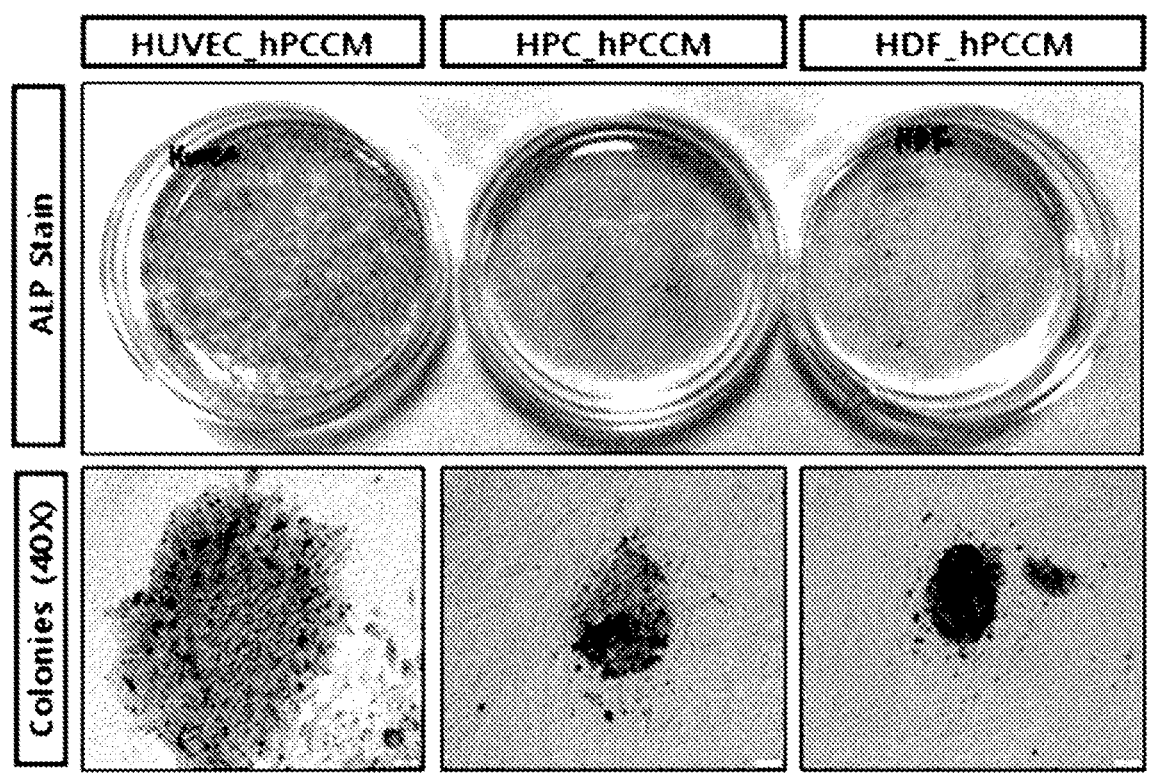
FIG. 2A shows images of cells that have been induced to dedifferentiate from endothelial cells, epithelial cells, and placenta cells and then have undergone alkaline phosphatase staining to examine characteristics of induced pluripotent stem cells (iPS).
Figure 2B:
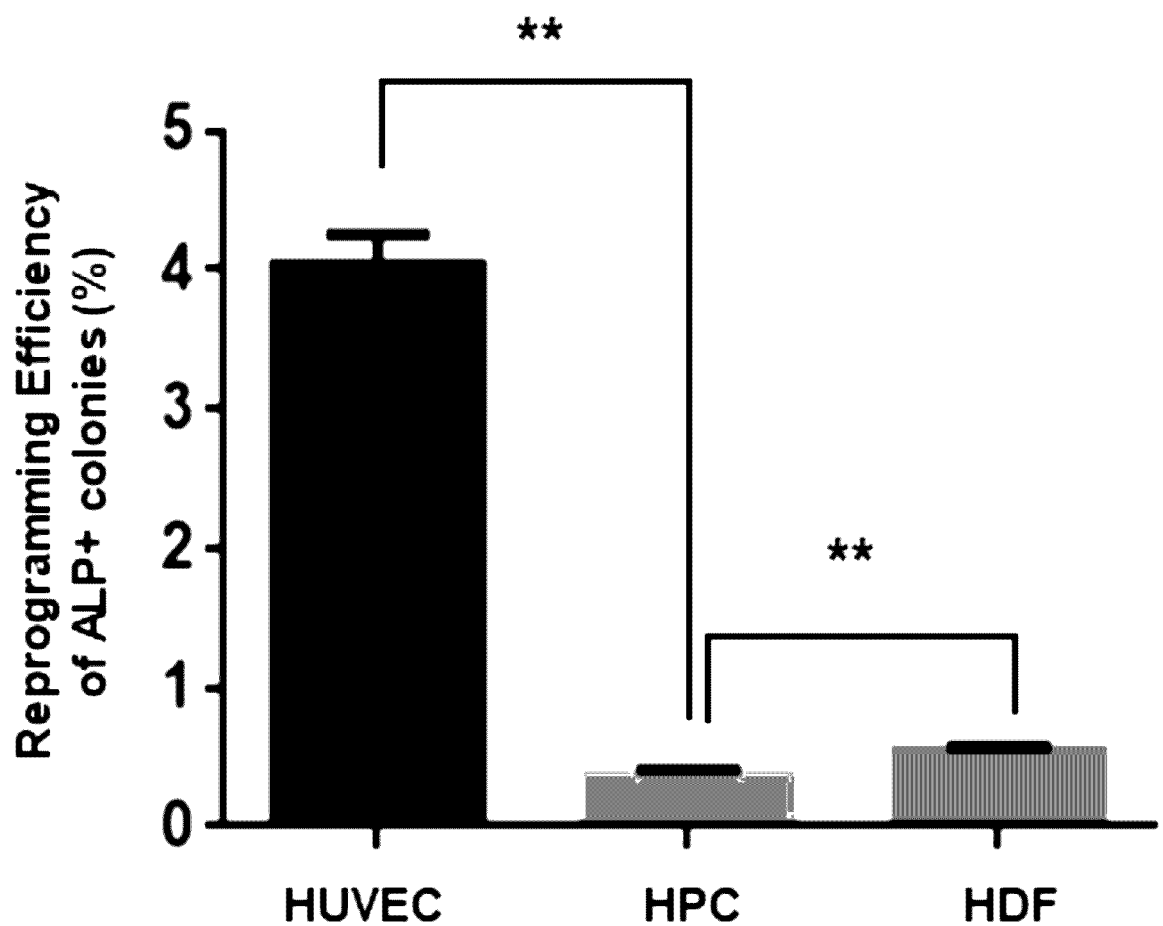
FIG. 2B is a graph showing characteristics of induced pluripotent stem cells that have dedifferentiated from endothelial cells, epithelial cells, and placenta cells and have undergone alkaline phosphatase staining.

As can be seen in Table 5 and FIGS. 2a and 2b, the dedifferentiation efficiency of human endothelial cells was 7 to 10 times as high as that of epithelial cells or placenta cells (**P=0.01).

TABLE 5

| Cell | Cell Inoculum (cells/mL) | Colony/well | Efficiency (%) |
|---|---|---|---|
| Human endothelial cell (HUVEC) | $1 \times 10^5$ | 4043 ± 0.21 | 4.043 |
| Placenta cell (HPC) | $1 \times 10^5$ | 380 ± 0.03 | 0.381 |
| Epithelial cell (HDF) | $1 \times 10^5$ | 553 ± 0.03 | 0.553 |

Example 3: Assay for Expression of CXCR2, mTOR, and β-Catenin in Stem Cells Dedifferentiated from Endothelial Cells, Epithelial Cells, and Placenta Cells The stem cells dedifferentiated from somatic cells in Example 1 were assayed for expression sites of CXCR2, mTOR, and β-Catenin, using immunofluorescence method. Previous studies reported that inhibition against CXCR2 and mTOR of human pluripotent stem cells decreases the activity of β-Catenin. As for human dedifferentiated stem cells cultured in a placenta-derived cell conditioned medium, the characteristics and growth of the human pluripotent stem cells are controlled through the CXCR2/mTOR/β-Catenin mechanism.

Therefore, it was expected and confirmed that during the formation of induced pluripotent stem cells with a placenta-derived cell conditioned medium, CXCR2 stimulation leads to the activity of dedifferentiated stem cells through the mTOR and β-Catenin mechanism.

In this regard, epithelial cells, endothelial cells, and placenta cells were used as human somatic cells. Sendai virus dedifferentiation factors (OCT4, SOX2, c-Myc, and KLF4, (Life Technologies, CytoTune™-iPS 2.0 Sendai Reprogramming Kit) were purchased and transfected at MOI (multiplicity of infection) of 5 for KOS, at MOI of 5 for c-Myc, and at MOI of 3 for Kif4 into the cells. After transfection, the cells were incubated for 7 days in growth media.

The growth medium for epithelial cells and placenta cells was DMEM (Dulbecco's modified Eagle's medium) supplemented with 10% fetal bovine serum (FBS), 100 U/ml penicillin, and 100 g/ml streptomycin and EBM-2 medium (LONZA, CC-3162) was purchased as the growth medium for endothelial cells.

The transfected somatic cells were transferred to a new culture vessel coated with 0.1% gelatin and supplied with a placenta-derived cell conditioned medium. While colonies were formed during incubation, fluorescence staining was performed every day.

Briefly, the cultured cells were fixed with 4% formalin at room temperature for 10 minutes, permeabilized with 0.1% Triton X-100 for 10 minutes, and then incubated overnight with a 1:1000 dilution of each of primary antibodies to CXCR2 (Abcam #ab14935), Nanog (Santacruz #sc-293121), β-Catenin (Thermo scientific #MA1-2001), and p-mTOR (Cell signaling #5536) at 4° C. On the next day, incubation with a secondary antibody at room temperature for one hour was followed by treatment with 4',6-diamin-dino-2-phenylindone (DAPI) for 5 minutes in a dark condition before observation by fluorescence microscopy.

Figure 3A:
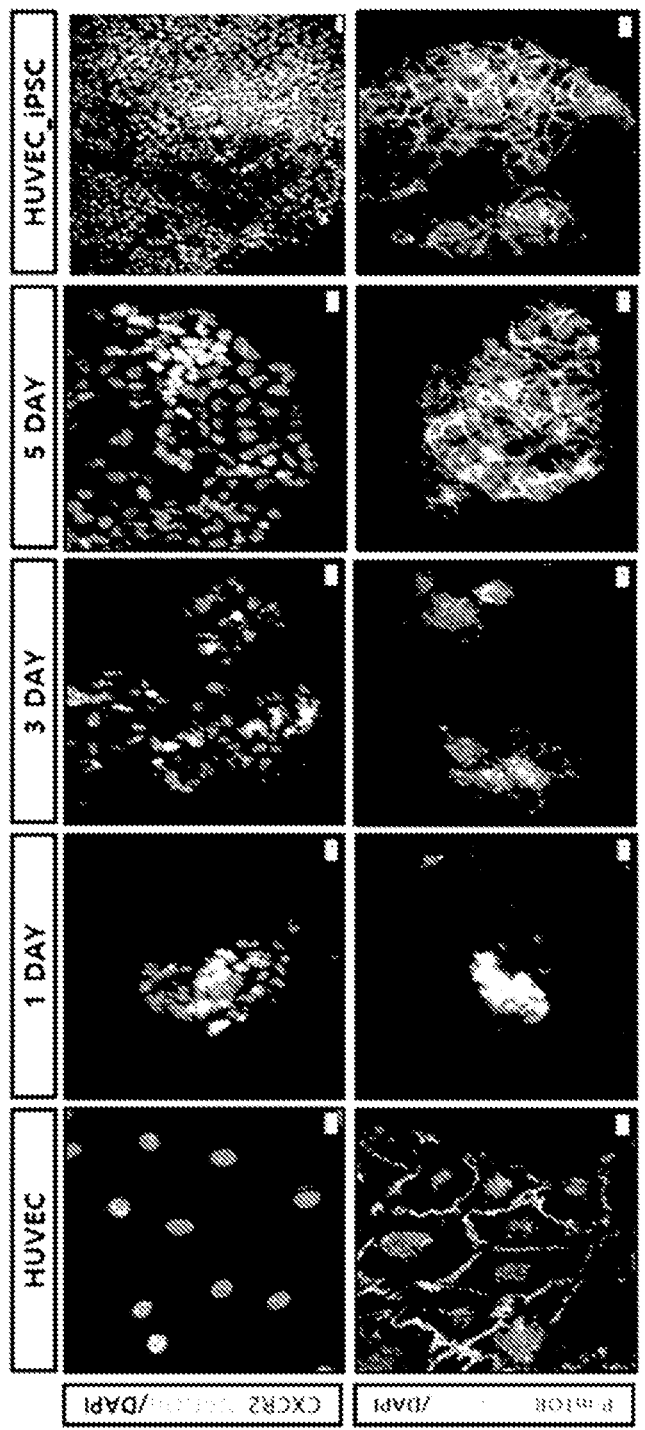
FIG. 3A shows immunofluorescence images of cells in the stem cell dedifferentiation process from human endothelial cells to colony formation.
Figure 3B:
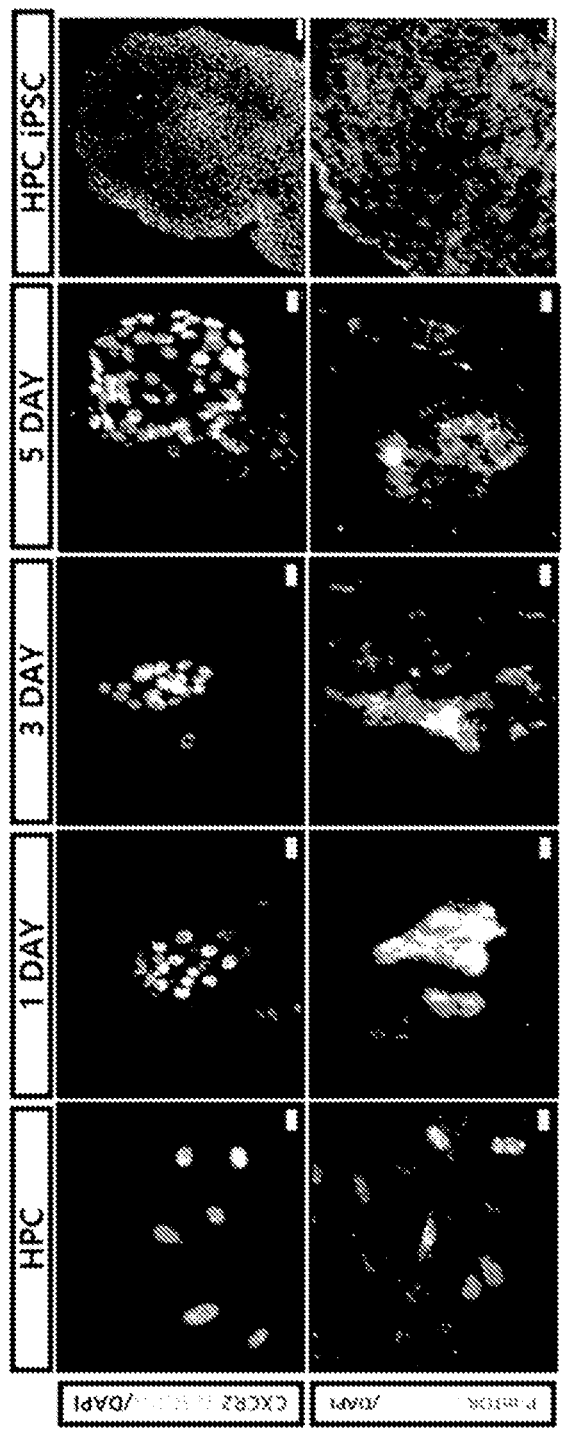
FIG. 3B shows immunofluorescence images of cells in the stem cell dedifferentiation process from human epithelial cells to colony formation.
Figure 3C:
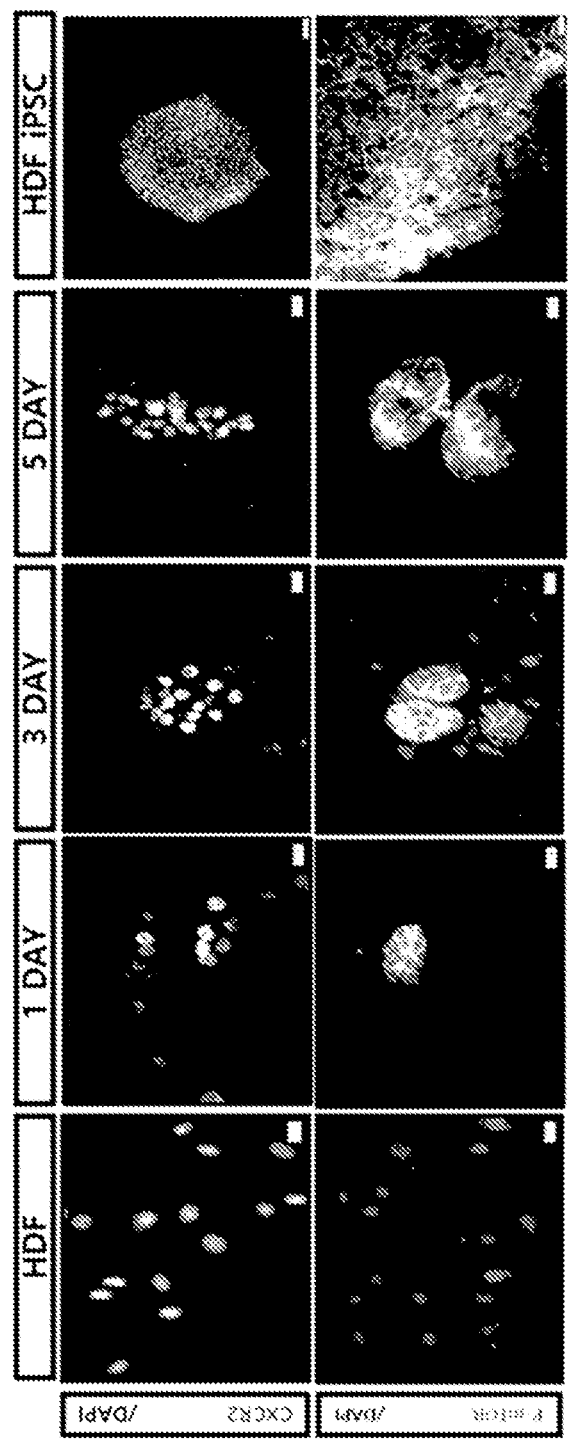
FIG. 3C shows immunofluorescence images of cells in the stem cell dedifferentiation process from human placenta cells to colony formation.

As can be seen in FIGS. 3a to 3c, CXCR2 stimulation to might be considered to allow the somatic cells to have the activity of dedifferentiated stem cells through the mTOR and β-Catenin mechanisms because only the cells which were formed into colonies during the dedifferentiation to stem cells expressed CXCR2, mTOR, and β-Catenin.

Example 4: shRNA-Induced Downregulation of CXCR2 Expression

When the endothelial cells expressing a high level of CXCR2 as in Example 2 were downregulated for CXCR2 expression by shRNA, the efficiency of dedifferentiated stem cells were found to significantly decrease.

For lentiviral infection, endothelial cells were seeded at a density of $1 \times 10^5$ cells/well into 12-well culture plates and incubated. On the next day, the cells were treated with a culture medium containing 6 mg/mL polybrene for 15 minutes and infected with lentivirus (CXCR2 shRNA lentiviral particles, Santacruz #sc-40028-V) having $1 \times 10^6$ TU/mL shRNA inserted thereto. After 24 hours, the medium was replaced with a cell growth medium free of polybrene. From the next day, selection was made of virus-infected cells for 4 to 7 days using 2 μg/mL puromycin. The cells thus harvested were assayed for CXCR2 expression.

Nucleic acid sequences of the CXCR2 shRNA lentiviral particles for use in lentiviral infection are as listed in Table 6, below.

TABLE 6

| SEQ ID NO: | Name | Sequence |
|---|---|---|
| 3 | sc-40028-VA | GATCCGTCTACTCATCCAATGTTATTCAAGAGATAACATTGGATGAGTAGACTTTTT |
| 4 | sc-40028-VB | GATCCCCTCAAGATTCTAGCTATATTCAAGAGATATAGCTAGAATCTTGAGGTTTTT |
| 5 | sc-40028-VC | GATCCGCCACTAAATTGACACTTATTCAAGAGATAAGTGTCAATTTAGTGGCTTTTT |

Cell groups which were respectively treated with control lentivirus and CXCR2 lentivirus and not treated with shRNA-inserted lentivirus were measured for CXCR2 expression at protein and RNA levels.

Briefly, for expression measurement at a protein level, cells were washed with chilled PBS and then stirred in a lysis buffer (20 mM KCl, 150 mM NaCl, 1% NP-40, 50 mM NaF, 1 mM DTT, 1 mM EGTA, 1× protease inhibitor, 10% glycerol, and 50 mM Tris-HCl, pH 7.5) for 15 minutes on ice. The lysate was centrifuged at 14,000 rpm and 4° C. for 15 minutes.

The protein concentration in the supernatant was determined using the Bradford assay (Bio-Rad Laboratories, Hercules, CA). Total protein (30 μg) was analyzed by sodium dodecyl sulfate-polyacrylamide gel electrophoresis and transferred onto a nitrocellulose membrane (GE Healthcare Life Sciences, Little Chalfont, UK). The membrane was incubated overnight with a 1:1,000 dilution of a primary antibody to CXCR2 (Abcam #ab65968) at 4° C. and then with a 1:2,000 dilution of a HRP-conjugated secondary antibody at room temperature for one hour. Signals were detected using ECL (GE Healthcare Life Sciences).

RNA levels were measured by real-time polymerase chain reaction. For normalization, use was made of GAPDH gene, and P values were used to determine statistical significance (*P=0.05). Primers for CXCR2 gene expression assay are as listed in Table 7, below.

TABLE 7

| SEQ ID NO: | Name | Sequence |
|---|---|---|
| 6 | Forward primer for CXCR2 expression assay | CAATGAATGAATGAATGGCTAAG |
| 7 | Reverse primer for CXCR2 expression assay | AAAGTTTTCAAGGTTCGTCCGTGTT |

Figure 4A:
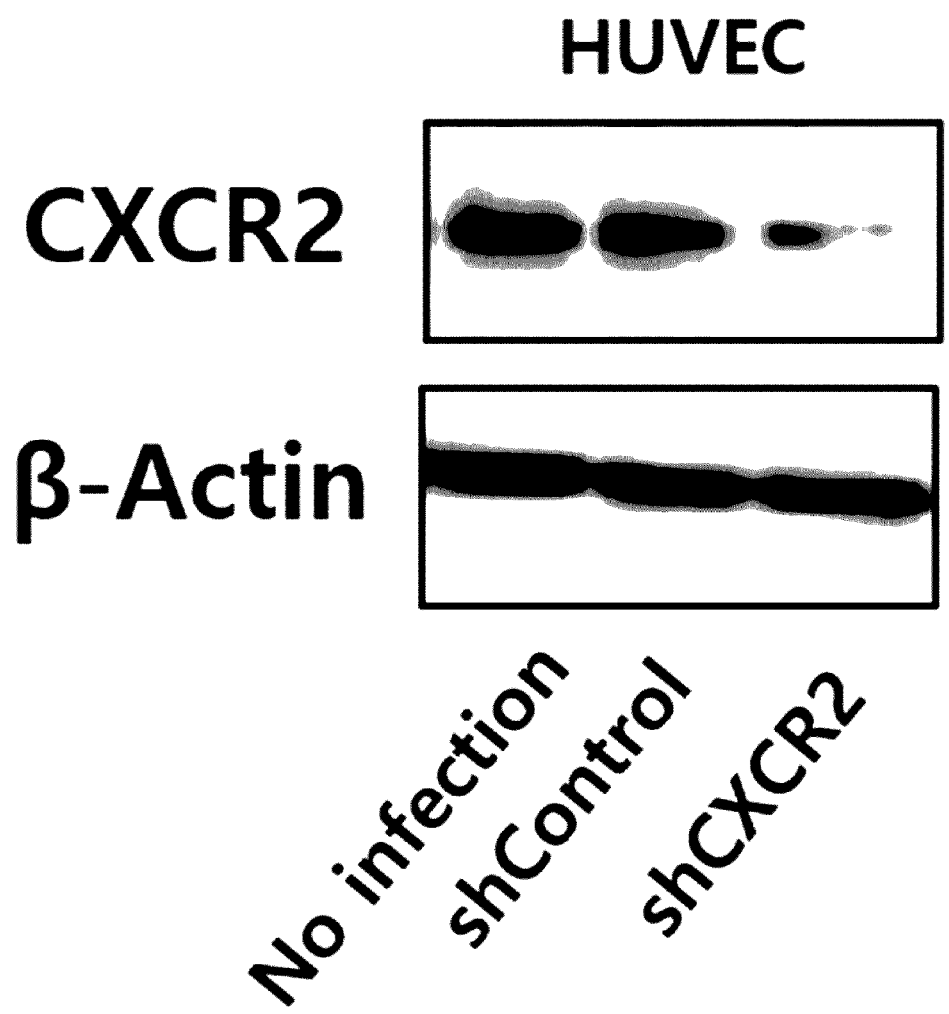
FIG. 4A shows CXCR2 (CXC chemokine receptor 2) protein levels in cells dedifferentiated from endothelial cells in which CXCR2 expression has been downregulated using shRNA, as measured by western blotting.
Figure 4B:
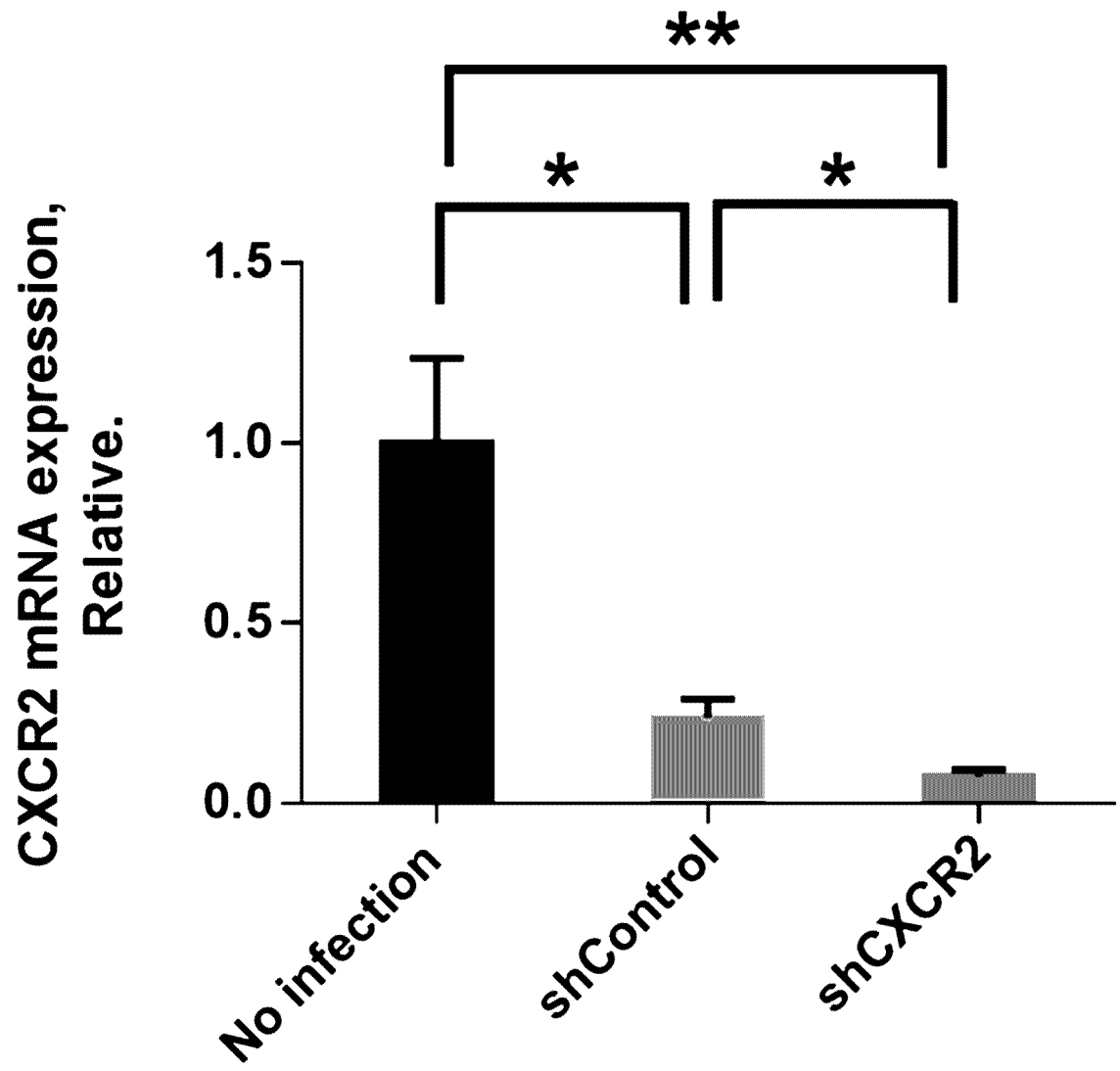
FIG. 4B is a graph showing CXCR2 RNA expression levels in cells dedifferentiated from endothelial cells in which CXCR2 expression has been downregulated using shRNA.

As can be seen in FIGS. 4a and 4b and Table 8, treatment with the shRNA-inserted lentivirus (shCXCR2) downregulated the expression of CXCR2 in the cells derived from endothelial cells.

TABLE 8

| | Control (No infection) | shControl | shCXCR2 |
|---|---|---|---|
| Relative mRNA expression level of CXCR2 | 1.00 | 0.26 | 0.08 |

Example 5: Reduction of Dedifferentiation Induction Efficiency by Downregulation of CXCR2 Expression Alkaline phosphatase (ALP) staining was conducted to examine efficiency of dedifferentiation from somatic cells to induced pluripotent stem cells upon the expression of CXCR2 as in Example 4.

Figure 5A:
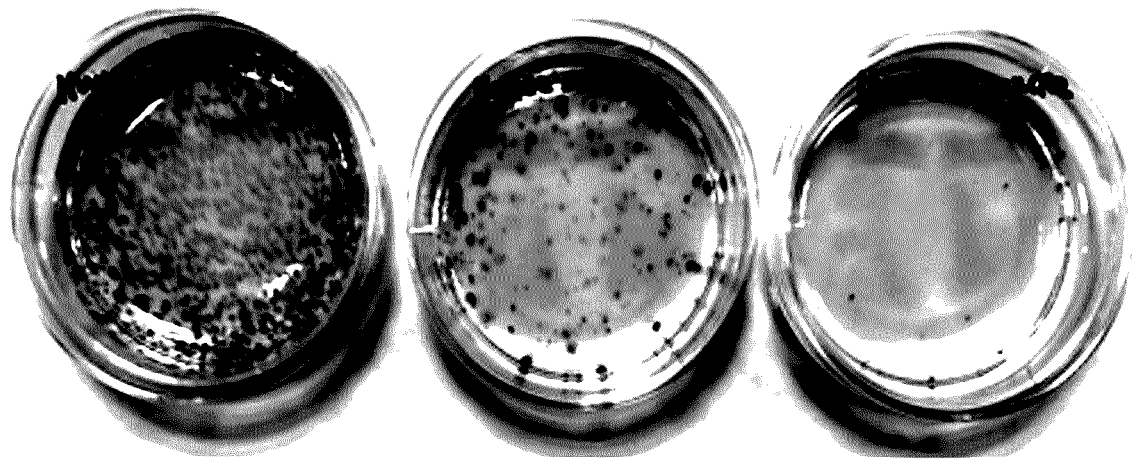
FIG. 5A shows images of induced pluripotent stem cells after endothelial cells in which CXCR2 expression was downregulated using shRNA have been induced to differentiate and undergone alkaline phosphatase staining to examine dedifferentiation efficiency.
Figure 5B:
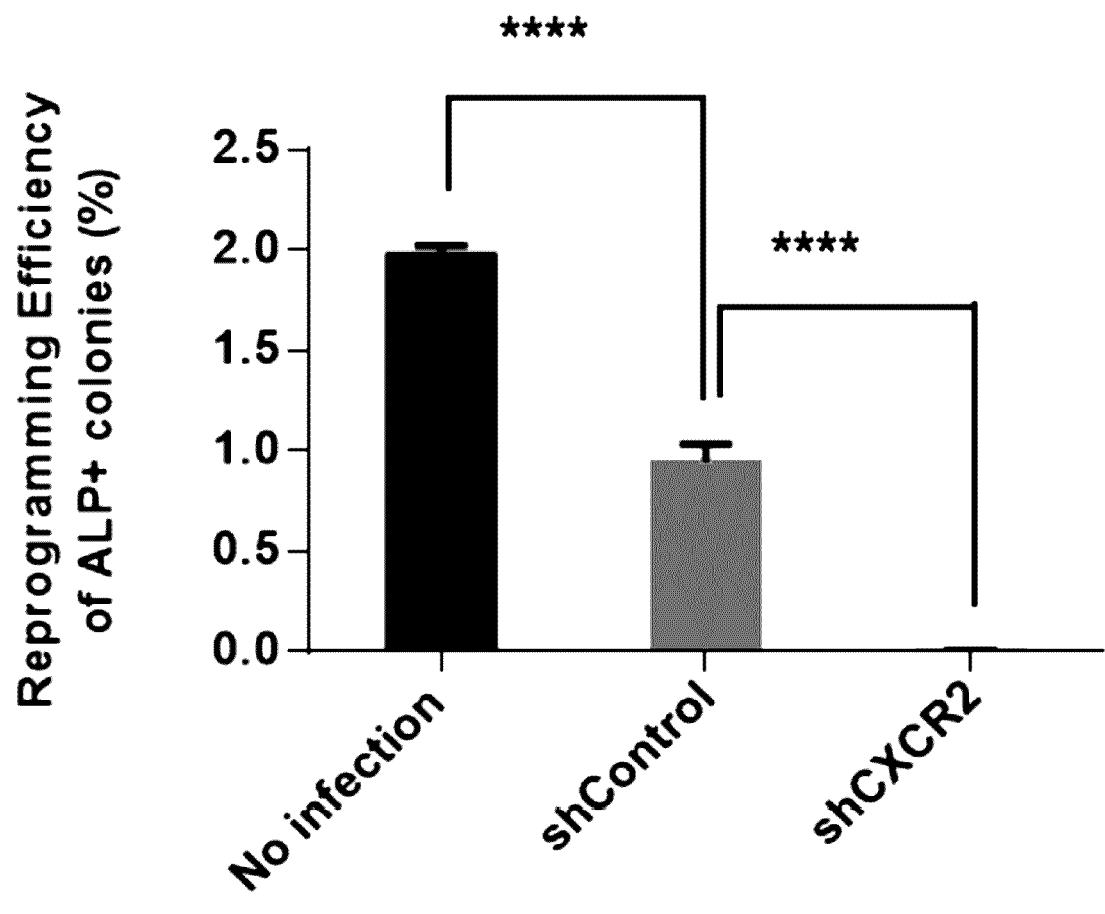
FIG. 5B is a graph showing efficiency of the dedifferentiation of induced pluripotent stem cells from endothelial cells in which CXCR2 expression has been downregulated using shRNA, as assayed by alkaline phosphatase staining.

As can be seen in Table 9 and FIGS. 5a and 5b, when endothelial cells were induced to dedifferentiate after the downregulation of CXCR2 expression therein by shCXCR2 lentivirus, efficiency of dedifferentiation to induced pluripotent stem cells was also reduced (****P=0.0001).

TABLE 9

| Infection condition | Cell inoculum | Colony/well | Efficiency(%) |
|---|---|---|---|
| Uninfected control | 1 × 10⁵ | 1,974 ± 50 | 1.973 |
| shControl lentivirus | 1 × 10⁵ | 946 ± 89.2 | 0.946 |
| shCXCR2 lentivirus | 1 × 10⁵ | 4 ± 2.70 | 0.004 |

Figure 5C:
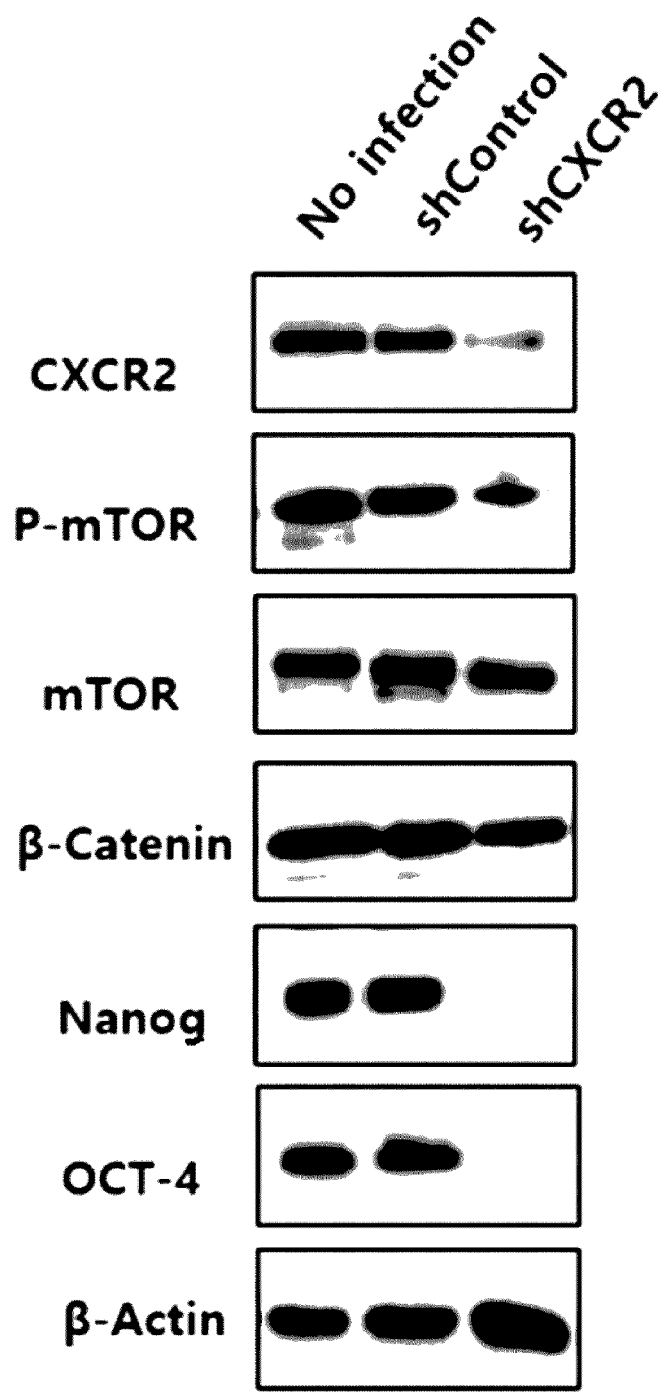
FIG. 5C shows expression levels of CXCR2, mTOR, and β-Catenin, and expression levels of markers of induced pluripotent stem cells upon dedifferentiation of induced pluripotent stem cells from endothelial cells in which CXCR2 expression has been downregulated using shRNA, as measured by western blotting.

As can be seen in FIG. 5c, when the expression of CXCR2 in endothelial cells was downregulated, the induced pluripotent stem cells dedifferentiated therefrom also decreased in expression levels of induced pluripotent stem cell markers as well as CXCR2, mTOR, and β-Catenin.

Example 6: Increase of Dedifferentiation Induction Efficiency by CXCR2 Overexpression In epithelial cells, CXCR2 was overexpressed using lentiviral activation particles.

Briefly, epithelial cells were seeded at a density of 1×10⁵ cells/well into 12-well plates. After 24 hours, the cells were incubated with 6 μg/ml polybrene for 15 minutes and infected with CXCR2 lentiviral activation particles (IL-8RB Lentiviral Activation Particles (h), SantaCruz, #sc-401404-LAC) at 10 MOI. On the next day, the medium was replaced with a polybrene-free medium and the cells were cultured overnight. Then, only CXCR2 lentiviral activation particle-infected cells were selected and cultured using 5 μg/mL puromycin.

Afterwards, the overexpression was monitored through western blot and real-time polymerase chain reaction. Expression levels of CXCR2 were measured in the same manner as in Example 4.

Figure 6A:
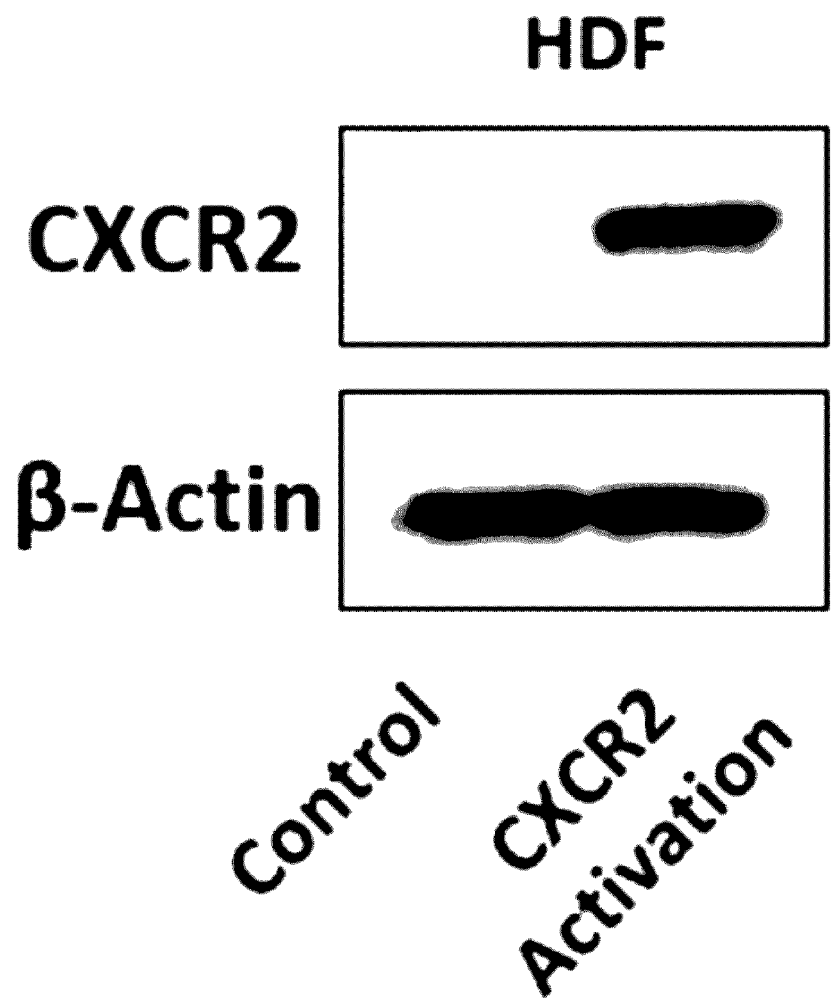
FIG. 6A shows CXCR2 protein levels in cells dedifferentiated from epithelial cells in which CXCR2 has been overexpressed using lentiviral activation particles, as measured by western blotting.
Figure 6B:
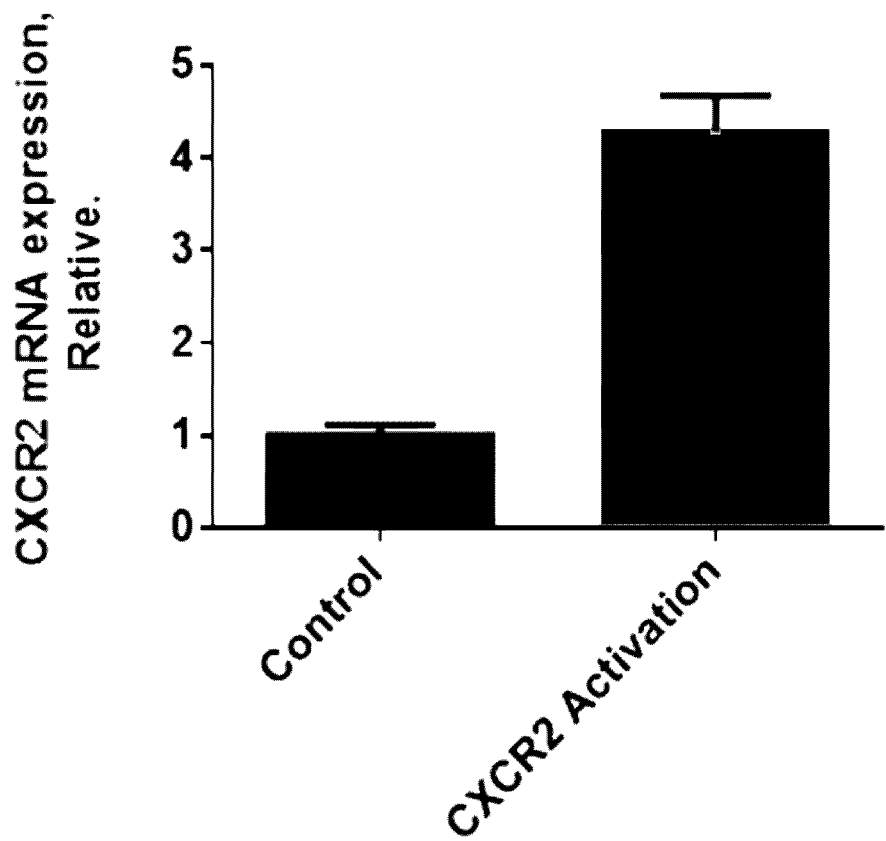
FIG. 6B is a graph of CXCR2 RNA expression levels in cells dedifferentiated from epithelial cells in which CXCR2 has been overexpressed using lentiviral activation particles.

As can be seen in FIGS. 6a and 6b and Table 10, the use of lentiviral activation particles upregulated the expression of CXCR2 in the cells derived from epithelial cells.

TABLE 10

| | Control | CXCR2 overexpression (CXCR2 Activation) |
|---|---|---|
| Relative mRNA expression level of CXCR2 | 1.00 | 4.29 |

In order to examine efficiency of dedifferentiation from somatic cells to induced pluripotent stem cells, a CXCR2-overexpressing group and a control group were each cultured in a commercially available pluripotent stem cell culture medium (TeSR) and a placenta-derived cell conditioned medium, separately, followed by conducting alkaline phosphatase staining as in Example 5.

Figure 6C:
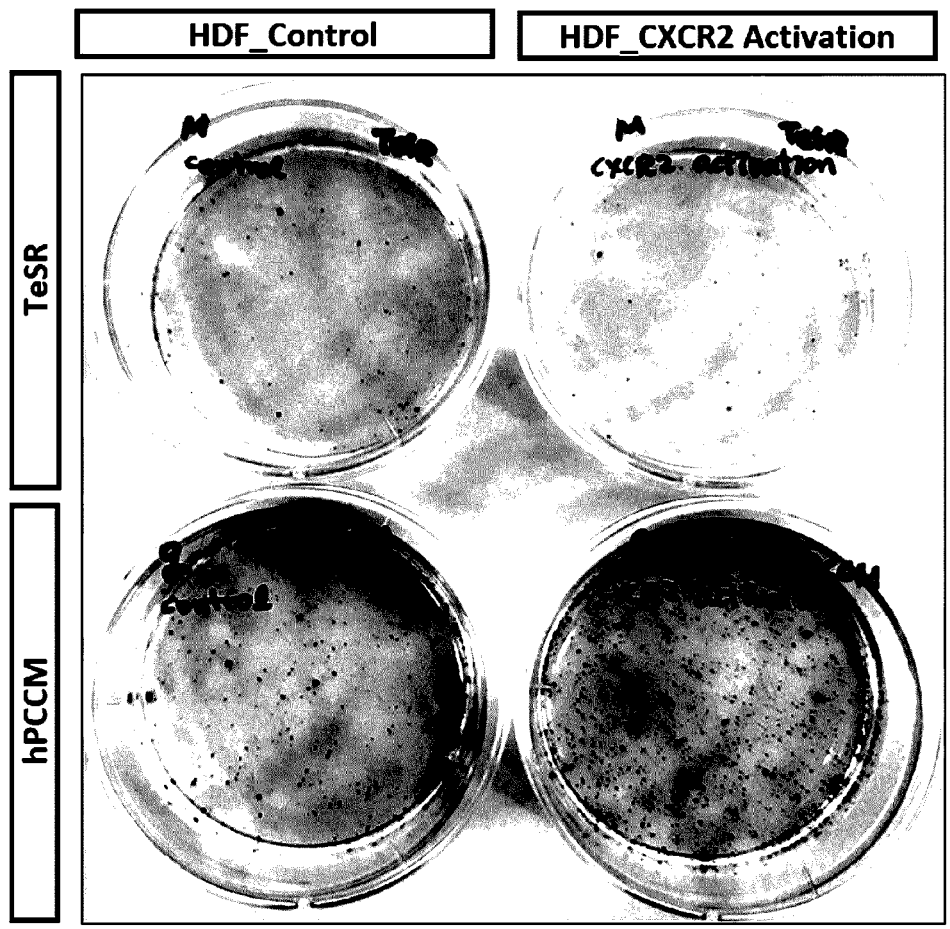
FIG. 6C shows images of induced pluripotent stem cells obtained by inducing dedifferentiation from epithelial cells in which CXCR2 has been overexpressed using lentiviral activation particles.
Figure 6D:
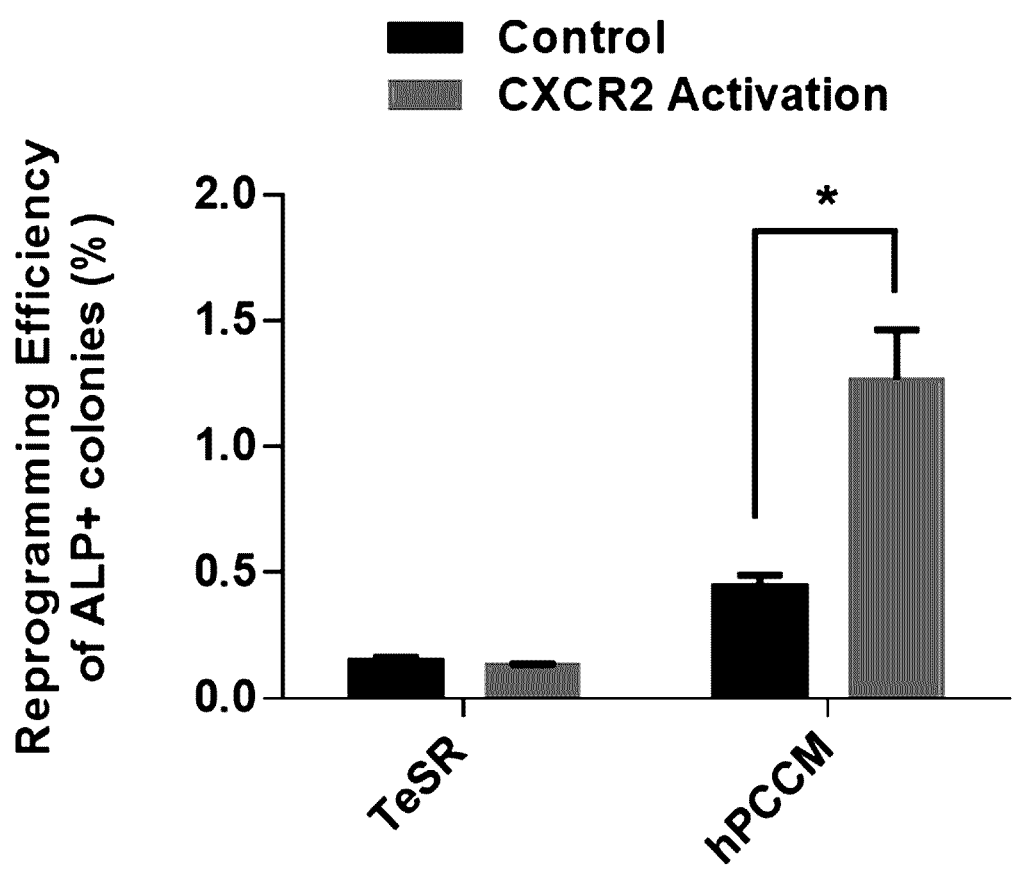
FIG. 6D is a graph showing counts of colonies of induced pluripotent stem cells obtained by inducing dedifferentiation from epithelial cells in which CXCR2 has been overexpressed using lentiviral activation particles.

As can be seen in Table 11 and FIGS. 6c and 6d, more induced pluripotent stem cells were dedifferentiated from epithelial cells in which CXCR2 had been overexpressed, compared to the control.

TABLE 11

| Infection condition | Cell inoculum | Colony/well | Efficiency (%) |
|---|---|---|---|
| TeSR_control | $1 \times 10^5$ | 151 ± 0.09 | 0.15 |
| TeSR_CXCR2 overexpressed | $1 \times 10^5$ | 132 ± 0.04 | 0.13 |
| Placenta-derived cell conditioned medium _control | $1 \times 10^5$ | 445 ± 0.25 | 0.45 |
| Placenta-derived cell conditioned medium_CXCR2 overexpressed | $1 \times 10^5$ | 1,267 ± 1.14 | 1.27 |

More dedifferentiated stem cells were established in the placenta-derived cell conditioned medium than in TeSR, with the highest peak of dedifferentiation induction in the group cultured in the placenta-derived cell conditioned medium.

INDUSTRIAL APPLICABILITY

The present disclosure pertains to a composition for inducing dedifferentiation from somatic cells to induced pluripotent stem cells (iPS) and a dedifferentiation induction method using the same and, more particularly, to a dedifferentiation induction composition which stimulates the human somatic cell receptor CXCR2 (CXC chemokine receptor 2) to promote or suppress dedifferentiation efficiency and a dedifferentiation induction method using same.

This application contains references to amino acid sequences and/or nucleic acid sequences which have been submitted herewith as the sequence listing text file. The aforementioned sequence listing is hereby incorporated by reference in its entirety pursuant to 37 C.F.R. 41.52(e).

What is claimed is:

1. A method for increasing efficiency of dedifferentiation from a somatic cell to an induced pluripotent stem cell (iPS), the method comprising:
   a somatic cell transformation step of increasing the expression of CXCR2 by transfection of CXCR2; and
   a somatic cell culturing step of culturing the transformed somatic cell,
   wherein the somatic cell is an epithelial cell and
   wherein the cell culturing step is performed in placenta-derived cell conditioned medium.

2. The method of claim 1, wherein the somatic cell transformation step employs a CRISPR/Cas nuclease system or lentiviral activation particles.

3. The method of claim 1, wherein the placenta-derived cell is a placenta-derived fibroblast-like cell that is isolated from human chorionic plate and cultured.

4. The method of claim 1, further comprising a stem cell isolation step of isolating a stem cell from a colony formed in the somatic cell culture step.

* * * * *